United States Patent [19]

Bertocchio et al.

[11] Patent Number: 4,983,769
[45] Date of Patent: Jan. 8, 1991

[54] PERFLUOROALKYLAMINE OXIDES AND USE OF THESE PRODUCTS IN FIRE EXTINGUISHING COMPOSITIONS

[75] Inventors: René Bertocchio, Vourles par Vernaison; Louis Foulletier, Oullins; André Lantz, Vernaison, both of France

[73] Assignee: P C U K Produits Chimiques Ugine Kuhlmann, Courbevoie, France

[21] Appl. No.: 147,667

[22] Filed: Jan. 25, 1988

Related U.S. Application Data

[63] Continuation of Ser. No. 567,613, Jan. 4, 1984, abandoned, which is a continuation of Ser. No. 428,672, Sep. 30, 1982, abandoned, which is a continuation of Ser. No. 226,557, Jan. 21, 1981, abandoned.

[30] Foreign Application Priority Data

Feb. 29, 1980 [FR] France .................................. 80 04519

[51] Int. Cl.⁵ ........................... A62C 1/10; A62C 1/12
[52] U.S. Cl. .......................................... 564/96; 252/2; 252/3; 252/307; 252/354; 252/355; 252/356; 252/357
[58] Field of Search ....................... 564/96, 209, 300; 252/2

[56] References Cited

U.S. PATENT DOCUMENTS

| | | | |
|---|---|---|---|
| 2,759,019 | 8/1956 | Brown et al. | 564/96 |
| 3,772,195 | 11/1973 | Francen | 252/8.05 |
| 4,090,967 | 5/1978 | Falk | 252/2 X |

FOREIGN PATENT DOCUMENTS

| | | | |
|---|---|---|---|
| 763644 | 7/1971 | Belgium | 564/96 |
| 1302612 | 1/1973 | United Kingdom | 564/96 |

Primary Examiner—Robert V. Hines
Attorney, Agent, or Firm—Pennie & Edmonds

[57] ABSTRACT

Perfluoroalkyl amine oxides of the following formula:

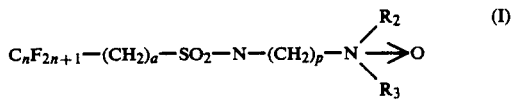

where $C_nF_{2n+1}$ is a straight or branched perfluorinated chain, n is a whole number from 1 to 20, a is a whole number from 2 to 10, p is a whole number from 0 to 10, $R_1$ is either a hydrogen atom or an alkyl radical having 1 to 6 carbon atoms, and $R_2$ and $R_3$ are alkyl radicals having 1 to 6 carbon atoms, and the use of the amine oxides as surface active agents particularly in fire extinguishing compositions.

9 Claims, No Drawings

PERFLUOROALKYLAMINE OXIDES AND USE OF THESE PRODUCTS IN FIRE EXTINGUISHING COMPOSITIONS

This application is a continuation of application Ser. No. 567,613, filed Jan. 4, 1984, abandoned, which is a continuation of application Ser. No. 428,672, filed Sept. 30, 1982, abandoned, which is a continuation of application Ser. No. 226,557, filed Jan. 21, 1981, abandoned.

TECHNICAL FIELD

The invention relates to novel perfluoroalkyl amine oxides of the following formula (I):

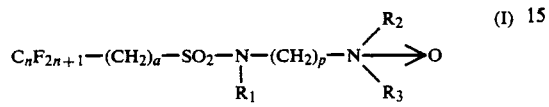
(I)

where $C_nF_{2n+1}$ is a straight or branched perfluorinated chain, n is a whole number from 1 to 20, a is a whole number from 2 to 10, p is a whole number from 0 to 10, $R_1$ is either a hydrogen atom or an alkyl radical having 1 to 6 carbon atoms, and $R_2$ and $R_3$ are alkyl radicals having 1 to 6 carbon atoms, and the use of the above amine oxides as surface active agents particularly in fire extinguishing compositions.

BACKGROUND OF THE INVENTION

Fire extinguishing compositions, particularly for extinguishing hydrocarbon fires, must have the ability to form a film on the surface of the fuel hydrocarbon and the effectiveness of such compositions depends a great deal on the spreading ability and the spread velocity of the film over the hydrocarbon surface. Minnesota Mining & Manufacturing Company's industrial product "LightWater FC 203" is an example of a commercial fire extinguishing composition. This composition contains a mixture of a fluorinated surfactant and a non-fluorinated surfactant. This product, however, only partially spreads over cyclohexane and gasoline at low fluorinated surfactant concentrations, and spreads relatively slowly on cyclohexane and gasoline even at high fluorinated surfactant concentrations.

SUMMARY OF THE INVENTION

This invention relates to novel perfluoroalkyl amine oxides of the following formula:

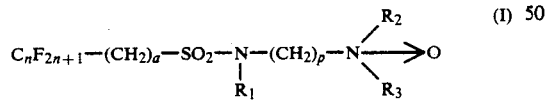
(I)

where $C_nF_2$, is a straight or branched perfluorinated chain, n is a whole number from 1 to 20, a is a whole number from 2 to 10, p is a whole number from 0 to 10, $R_1$ is either a hydrogen atom or an alkyl radical having 1 to 6 carbon atoms, and $R_2$ and $R_3$ are alkyl radicals having 1 to 6 carbon atoms; and to the use of the above amine oxides as surface active agents in fire extinguishing compositions. The use of the novel amine oxides together with non-fluorinated surface active agents, such as those described in U.S. Pat. No. 3,562,156 results in a fire extinguishing composition having a considerably improved spread velocity at both low and high amine oxide concentrations on cyclohexane and gasoline over those exhibited by the commercial product FC 203. The amine oxide composition also spreads completely over hexane at a concentration of 86 mg fluorine per 100 cm$^3$.

Products where a=2, p=3, $R_2$ and $R_3$ are methyl radicals, and $R_1$ is hydrogen or a methyl radical are especially advantageous as surface active agents in fire extinguishing compositions.

DETAILED DESCRIPTION OF THE INVENTION

These new amine oxides can be prepared by standard methods of amine oxide preparation, for example, by the reaction of corresponding amines with hydrogen peroxide (see, for example, Kirk Othmer, 3rd ed., v. 2, pp. 259 to 271).

The amines useful for the preparation of the amine oxides of this invention have the general formula (II):

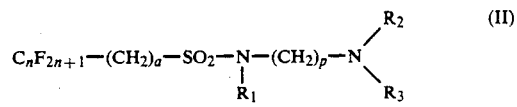
(II)

where a, p, n, $R_1$, $R_2$, and $R_3$ are the same as above given in formula (I) and have been described previously, for example, in French Pat. No. 2,088,594.

These sulfamidoamines can also be used as raw materials for the manufacture of fluorinated surface active agents of the cationic or amphoteric kind. Thus, French Pat. No. 2,084,888 (U.S. Pat. No. 3,721,706); 2,088,941; 2,128,028 and 2,390,426 describe surface active agents obtained by quaternization of these amines with alkyl halides, that is cationic surface active agents and beta-ines obtained by quaternization of the same amines with halo-carboxylic acid salts, saturated aliphatic lactones or α-ethylenic acids. The three formulas herebelow represent characteristic examples of these different products:

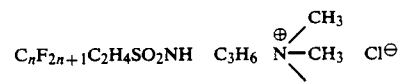

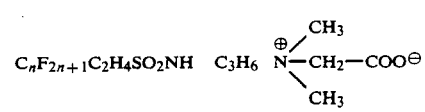

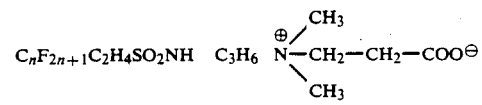

These fluorinated surface active agents notably lower the surface tension of aqueous solutions and thus can be used as wetting, foaming, emulsifying and dispersing agents. Because of the significant reduction of the surface tension in water, these products are also useful for making surface active compositions capable of serving as a base in the preparation of fire-extinguishing mixtures for fighting hydrocarbon fires.

The applicants have established that the amine oxides of this invention have surface active properties that are significantly superior to those of the cationic or amphoteric products cited above. These differences are illustrated by the results of measurements of reduced surface tension in the aqueous solutions shown in Table I.

TABLE I

| No. | | Surface Tension of Aqueous Solutions of 0.1% Fluorinated Products in dynes/cm at 20° C. |
|---|---|---|
| 1. | $C_6F_{13}C_2H_4SO_2NHC_3H_6\overset{\oplus}{N}(CH_3)_2{-}CH_3\ Cl^{\ominus}$ | 27 |
| 2. | $C_6F_{13}C_2H_4SO_2NHC_3H_6\overset{\oplus}{N}(CH_3)_2{-}CH_2{-}COO^{\ominus}$ | 17 |
| 3. | $C_6F_{13}C_2H_4SO_2NHC_3H_6\overset{\oplus}{N}(CH_3)_2{-}CH_2{-}CH_2{-}COO^{\ominus}$ | 17 |
| 4. | $C_6F_{13}C_2H_4SO_2N(CH_3)C_3H_6\overset{\oplus}{N}(CH_3)_2{-}CH_2{-}COO^{\ominus}$ | 16.8 |
| 5. | $C_6F_{13}C_2H_4SO_2NHC_3H_6N(CH_3)_2{\rightarrow}O$ | 13.4 |

The excellent surface active properties of the amine oxides of this invention are also evident from their ability to form a film on the surface of a hydrocarbon when an aqueous surface active solution is deposited on the hydrocarbon. French Pat. Nos. 1,405,794 and 2,009,827 (U.S. Pat. No. 3,562,156) teach that surface active aqueous solutions which form a film on the surface of hydrocarbons can be used as fire-extinguishers.

The filming ability of a surface active aqueous solution is connected to its surface tension $\gamma_B$, the surface tension of the hydrocarbon $\gamma_A$, and the interfacial tension $\gamma_{AB}$ between the two mediums by the formula:

$$S=\gamma_A-(\gamma_B+\gamma_{AB})$$

The filming ability improves as the spreading coefficient S acquires a higher positive value. Thus, the surface active aqueous solutions spread all the better because their surface tension and their interfacial tension in relation to the hydrocarbon have lower values.

The efficacy of filming fire-extinguishing agents depends especially on the speed with which the film spreads on the surface of a hydrocarbon. This can be evaluated by the spread velocity test, that is, the time spent by a determined volume of surface active solution to completely cover a particular hydrocarbon surface.

This speed can be determined in the following manner: A 120 mm diameter glass dish is half filled with the relevant hydrocarbon. A surface active solution of 0.1 cm³ is deposited in the center of the hydrocarbon surface. The difference in reflectivity allows one to follow the progress of the fluorinated film and thus to measure the necessary time, in seconds, to obtain the complete covering of the surface. This spread test is achieved with surface active solutions having different concentrations (expressed in mg of fluorine per 100 cm³ of solution) in soft water and sea water. Three reference hydrocarbons are used, having different surface tensions:

| cyclohexane | $_A=$ 25.3 dynes/cm at 20° C. |
|---|---|
| gasoline F | $_A=$ 22.4 dynes/cm at 20° C. |
| n hexane | $_A=$ 18.4 dynes/cm at 20° C. |

In the case where the referred to hydrocarbon is gasoline F or hexane on which the spread is more difficult to obtain than on cyclohexane, the volume of the solution deposited on the solvent is 0.5 cm³.

The sea water used for these tests is synthetic sea water having the following composition:

| 1.1% | $MgCl_2.6\ H_2O$ |
|---|---|
| 0.16% | $CaCl_2.2\ H_2O$ |
| 0.4% | $Na_2SO_4$ |
| 2.5% | NaCl |
| 95.84% | Distilled Water |

The amine oxide corresponding to product No. 5 of Table I has excellent filming properties illustrated by the spread velocity test and the results are shown in Table II. The time necessary to obtain complete spreading is shown in seconds and the letter p means that there are only partial spreading.

TABLE II

| Concentration of the Fluorinated Surface Active Agent expressed in mg Fluorine/ 100 cm³ | Soft Water Solution | | Sea Water Solution | |
|---|---|---|---|---|
| | Cyclo-hexane | Gasoline F | Cyclo-hexane | Gasoline F |
| 86 | 11.5 | 19.5 | 22.5 | 36.5 |
| 69 | 14 | 21 | 26 | 43 |
| 52 | 18.5 | 27.5 | 40 | p |

TABLE II-continued

| Concentration of the Fluorinated Surface Active Agent expressed in mg Fluorine/ 100 cm$^3$ | Soft Water Solution | | Sea Water Solution | |
|---|---|---|---|---|
| | Cyclo-hexane | Gasoline F | Cyclo-hexane | Gasoline F |
| 34 | p | p | p | — |

Although there is no spreading on hexane, even at a concentration of 250 mg fluorine per 100 cm$^3$ of solution, these results can be considered excellent since in practice most of the fluorinated surface active agents described in the literature do not form desirable films on hydrocarbons whose surface tension is lower than that of cyclohexane. Thus, products Nos. 2 and 3 in Table I do not form any film on gasoline F and do not spread completely over cyclohexane except in concentrations of 86 and 69 mg fluorine per 100 cm$^3$ and in 40 to 60 seconds.

The amphoteric derivatives such as products Nos. 2, 3 and 4 of Table I are, therefore, not useable alone in fire-extinguishing compositions. However, it is possible to use them for this application in conjunction with other fluorinated surface active agents, for example. Such compositions are described in French Pat. No. 2,308,674 (U.S. Pat. No. 4,069,158). It is also possible to use them together with non-fluorinated surface active agents as those described in French Pat. No. 2,009,827 (U.S. Pat. No. 3,562,156). The addition of a non-fluorinated surface active agent to an aqueous fluorinated surface active solution, in effect, lowers the interfacial tension between the aqueous solution and the hydrocarbon and increases the spreading coefficient. Different types of hydrocarbon surface active agents can thus be used to improve the spread of aqueous fluorinated surface active agents on hydrocarbons, and the ionic and nonionic surface active agents can provide good results as well. This action of fluorinated and non-fluorinated surface active agents can be shown through the filming ability in Table III of an aqueous composition made up of: 1 part of the amphoteric compound

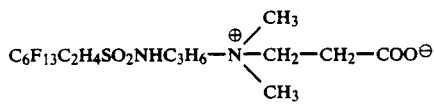

and 3 parts of the nonionic surface active agent sold under the trademark TRITON × 100 (ethoxylated octylphenol having 10 ethylene oxide groups) by Rohm & Haas Company).

TABLE III

| Concentration of the Fluorinated Surface Active Agent expressed in mg Fluorine/ 100 cm$^3$ | Soft Water Solution | | Sea Water Solution | |
|---|---|---|---|---|
| | Cyclo-hexane | Gasoline F | Cyclo-hexane | Gasoline F |
| 86 | 3.5 | 5 | 1.5 | 2.5 |
| 69 | 3 | 10 | 1.5 | 2.5 |
| 52 | 5 | 19 | 2 | 3.5 |
| 34 | 9 | p | 4 | 9.5 |
| 17 | p | — | p | p |

At a concentration of 86 mg fluorine per 100 cm$^3$ of solution, the aforesaid composition forms a film on hexane but this film only gives a very partial spread.

This improvement of the spreading properties by the addition of a non-fluorinated surface active agent is exceptionally good when using amine oxides according to this invention and, even under these conditions, the filming properties of amine oxides are very superior to those of the fluorinated surface active agents cited above, alone or in combination with non-fluorinated surface active agents. Thus, an aqueous composition made up of:

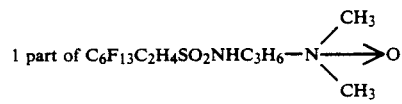

3 parts of TRITON × 100 provides the spreading results shown in Table IV.

TABLE IV

| Concentration of Fluorine Surface Active Agent Expressed in mg of Fluorine/100 cm$^3$ | Soft Water Solution | | Sea Water Solution | |
|---|---|---|---|---|
| | Cyclo-hexane | Gasoline F | Cyclo-hexane | Gasoline F |
| 86 | 1 | 1 | 1.5 | 1.5 |
| 69 | 1 | 1 | 1.5 | 1.5 |
| 52 | 1 | 1.5 | 2 | 2 |
| 34 | 1.5 | 1.5 | 4 | 4 |
| 17 | 11.5 | 11 | 15 | 10 |

A comparison of Tables III and IV confirms the significant superiority of the amine oxides of this invention, especially since the last composition (as reported in Table IV) containing amine oxide and the nonionic surface active agent spreads completely over hexane at a concentration of 86 mg fluorine per 100 cm$^3$ in 7.5 seconds in a soft water medium and in 23 seconds in a sea water medium. The identical composition with the amphoteric surface active agent No. 3 in Table I in place of amine oxide does not result in a complete spread over hexane at the same concentration.

The superiority of the amine oxides over the amphoteric derivatives is even more remarkable because these latter products are also fluorinated surface active agents that result in good extinguishers. Minnesota Mining & Manufacturing Company's industrial product "Light Water FC 203", which is probably one of the most frequently used compositions in this field, has, for example, at equal fluorine strengths, slightly lower filming properties than those of the amphoteric derivative with TRITON × 100. Also, its spreading results (Table V) are very clearly inferior to those of the amine oxides (Table IV).

TABLE V

| Concentration of FC 203 Expressed in mg of Fluorine 100 cm$^3$ | Soft Water Solution | | Sea Water Solution | |
|---|---|---|---|---|
| | Cyclo-hexane | Gasoline F | Cyclo-hexane | Gasoline F |
| 86 | 5.5 | 6.5 | 5 | 8.5 |
| 69 | 6.5 | 11.5 | 7 | 11 |
| 52 | 17 | 27.5 | 13 | 19 |
| 34 | p | p | 35 | 50 |
| 17 | — | — | p | p |

Thus, the amine oxides of this invention are very useful in the field of fire extinguishing agents of the AFFF type ("Aqueous Foam Forming Film") especially when use together with other fluorinated or non-fluorinated surface active agents. In addition, the concentrate for the extinguisher can contain other known additives, such as foaming (hydrocarbon surface active) agents, antigels, solvents, foam stabilizers, chelating agents, corrosion inhibitors and electrolytes. The foam generating compound can also be made up of protein hydrolyzates since these new surface active agents, by reason of their chemical nature, are particularly compatible with protein emulsifiers.

For the purpose of further disclosures of fluorinated and non-fluorinated surface active agents that can be used in combination with the amine oxides of this invention, U.S. Pat. Nos. 4,069,158 of Jan. 17, 1976 and 3,562,156 of Feb. 9, 1971 are incorporated herein by reference.

The following examples illustrate the invention:

EXAMPLE 1

In a reactor containing 512 g of

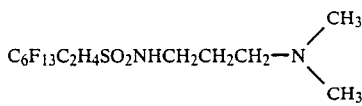

500 g of 95% ethanol, 200 g water and 100 g of 70% hydrogen peroxide are introduced under agitation at 35° C. The mixture is then maintained at this temperature and under agitation for 24 hours. Then 1 g of active carbon is introduced and it is heated for two hours under reflux so that the condensed liquid flows back. Then, the mixture is filtered, and by evaporation under a vacuum, 547 g of a white solid are obtained, melting with decomposition at between 135° and 138° C., and identified by mass spectrometry, by infrared spectrometry and by nuclear magnetic resonance as being the hydrated amine oxide

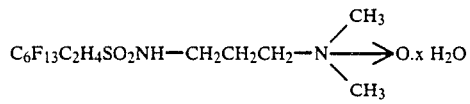

By titration of this product with hydrochloric acid before and after transformation of the residual amine into a quaternary ammonium salt by reaction with methyl iodide, the amount of non-transformed tertiary amine is determined to be less than 1% and the amount of amine oxide to be 88.5%.

The surface tensions of the aqueous solutions of this product at 20° C. are as follows:

| 1000 ppm Amine Oxide | 13.4 dynes/cm |
| 100 ppm Amine Oxide | 13.4 dynes/cm |
| 10 ppm Amine Oxide | 29 dynes/cm |

The good spreading properties of this amine oxide are shown above in Tables II and IV.

EXAMPLE 2

With the same method as that described in Example 1, but using

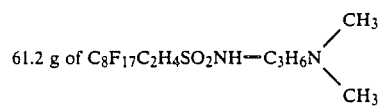

50 g of 95% ethanol, 20 g water, and 20 g of 70% $H_2O_2$, 66 g of hydrated amine oxide are obtained having the formula

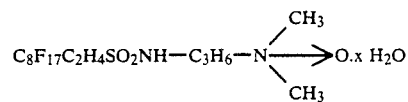

Titration showed 1% non-transformed residual amine and 85% amine oxide.

The surface tensions of the aqueous solutions of this product, at 20° C., are as follows:

| 1000 ppm Amine Oxide | 17 dynes/cm |
| 100 ppm Amine Oxide | 21.9 dynes/cm |
| 10 ppm Amine Oxide | 24.8 dynes/cm |

EXAMPLE 3

With the same process as that in Example 1, but using

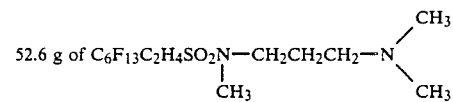

50 g of 95% ethanol, 20 g of water, and 10 g of 70% $H_2O_2$, 57 g of hydrated amine oxide are obtained having the formula

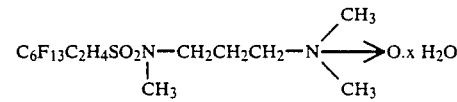

The surface tensions of the aqueous solutions of this product, at 20° C., are as follows:

| 1000 ppm Amine Oxide | 16.3 dynes/cm |
| 100 ppm Amine Oxide | 16.3 dynes/cm |

This product of Example 3 was tested as a fire extinguishing formulation using the spread test described above, in a mixture with 3 parts of TRITON×100 for 1 part of the amine oxides. The results obtained are set forth in Table VI:

TABLE VI

| Amine Oxide Concentration | Soft Water Solution | | Sea Water Solution | |
| --- | --- | --- | --- | --- |
| Expressed in mg fluorine/100 cm$^3$ | Cyclo-hexane | Gasoline F | Cyclo-hexane | Gasoline F |
| 86 | 1 | 1.5 | 1 | 1 |
| 69 | 1 | 2 | 1 | 1 |
| 52 | 1 | 2 | 1.5 | 1 |
| 34 | 2 | 4.5 | 2.5 | 2.5 |
| 17 | 15 | p | 14 | 17 |

EXAMPLE 4

With the same process as that described in Example 1, but using 50 g of 95% ethanol, 20 g of water, 10 g of 70% $H_2O_2$, and

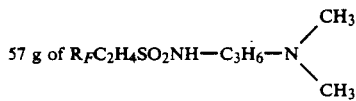

57 g of $R_FC_2H_4SO_2NH-C_3H_6-N(CH_3)_2$ the corresponding amine oxides are formed.

The sulfamidamine used for this procedure is a mixture of different homologs, where the fluorinated chain $R_F$ varies from 4 to 14 carbon atoms. The composition by weight of the product used is as follows:

| | | |
|---|---|---|
| $C_4F_9$ | Derivative | 1% |
| $C_6F_{13}$ | Derivative | 50% |
| $C_8F_{17}$ | Derivative | 31% |
| $C_{10}F_{21}$ | Derivative | 10% |
| $C_{12}F_{25}$ | Derivative | 4% |
| $C_{14}F_{29}$ | Derivative | 2% | and the average molecular mass 570.

61 g of a white solid are obtained, identified as being hydrated amine oxides with the formula:

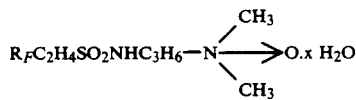

$R_FC_2H_4SO_2NHC_3H_6-N(CH_3)_2 \rightarrow O \cdot x\ H_2O$

Titration showed 82% amine oxides and 1.6% free amine.

The surface tensions of the aqueous solutions of this product, at 20° C., are as follows:

| | |
|---|---|
| 1000 ppm | 17 dynes/cm |
| 100 ppm | 21.9 dynes/cm |
| 10 ppm | 24.8 dynes/cm |

The results of the test for spreading velocity, as described above, for a mixture of 1 part of the amine oxide of this Example 4 and 3 parts TRITON×100 are set forth in Table VII.

TABLE VII

| Amine Oxide Concentration | Soft Water Solution | | Sea Water Solution | |
|---|---|---|---|---|
| Expressed in mg Fluorine/100 cm³ | Cyclo-hexane | Gasoline F | Cyclo-hexane | Gasoline F |
| 84 | 2 | 4 | 4.5 | 7 |
| 69 | 3 | 4.5 | 7.5 | 9 |
| 52 | 4 | 7.5 | 10.5 | 13.5 |
| 34 | 7.5 | 12.5 | 26.5 | 29 |

TABLE VII-continued

| Amine Oxide Concentration | Soft Water Solution | | Sea Water Solution | |
|---|---|---|---|---|
| Expressed in mg Fluorine/100 cm³ | Cyclo-hexane | Gasoline F | Cyclo-hexane | Gasoline F |
| 17 | p | p | p | p |

We claim:

1. A surface-active composition containing, as a surface-active agent, a perfluoroalkyl amine oxide having the formula:

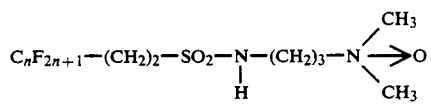

$$C_nF_{2n+1}-(CH_2)_2-SO_2-N(H)-(CH_2)_3-N(CH_3)_2 \rightarrow O$$

where n is equal to 6 or 8.

2. The composition of claim 1 wherein n is 6.
3. A composition useful for suppressing vaporization of liquid hydrocarbons which comprises water and perfluoroalkyl amine oxide having the formula:

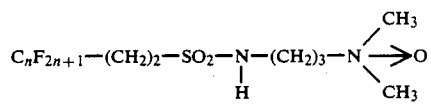

$$C_nF_{2n+1}-(CH_2)_2-SO_2-N(H)-(CH_2)_3-N(CH_3)_2 \rightarrow O$$

where n is equal to 6 or 8.

4. The composition of claim 3 wherein n is 6.
5. A composition for suppressing vaporization of liquid hydrocarbons which comprises water, a perfluoroalkyl amine oxide having the formula:

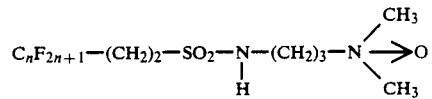

$$C_nF_{2n+1}-(CH_2)_2-SO_2-N(H)-(CH_2)_3-N(CH_3)_2 \rightarrow O$$

where n is equal to 6 or 8, and a non-fluorinated surfactant or a fluorinated surfactant which is different from said amine oxide.

6. The composition of claim 5 wherein n is 6.
7. The composition of claim 5 in which the non-fluorinated surfactant is an ethylene oxide based surfactant.
8. A method for extinguishing hydrocarbon fires which utilizes a composition having considerably improved spreading velocity at both low and high amine oxide concentrations on cyclohexane and gasoline which contains novel perfluoroalkyl amine oxides of the following formula:

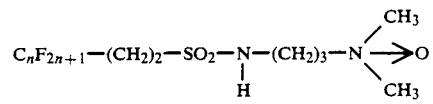

$$C_nF_{2n+1}-(CH_2)_2-SO_2-N(H)-(CH_2)_3-N(CH_3)_2 \rightarrow O$$

where n is equal to 6 or 8.

9. The method of claim 8 wherein n is 6.

* * * * *